(12) United States Patent
Ahlers et al.

(10) Patent No.: US 9,878,962 B2
(45) Date of Patent: Jan. 30, 2018

(54) PROCESS AND PLANT FOR PRODUCING OLEFINS FROM OXYGENATES

(71) Applicant: L'Air Liquide, Societe Anonyme pour l'Etude et l'Exploitation des Procedes Georges Claude, Paris (FR)

(72) Inventors: Bernd Ahlers, Dietzenbach (DE); Martin Gorny, Eschborn (DE); Hermann Bach, Heiligenroth (DE)

(73) Assignee: L'AIR LIQUIDE SOCIÉTÉ ANONYME POUR L'ÉTUDE ET L'EXPLOITATION DES PROCEDES GEORGE CLAUDE, Paris (FR)

( * ) Notice: Subject to any disclaimer, the term of this patent is extended or adjusted under 35 U.S.C. 154(b) by 46 days.

(21) Appl. No.: 14/654,271

(22) PCT Filed: Dec. 3, 2013

(86) PCT No.: PCT/EP2013/075441
§ 371 (c)(1),
(2) Date: Jun. 19, 2015

(87) PCT Pub. No.: WO2014/095360
PCT Pub. Date: Jun. 26, 2014

(65) Prior Publication Data
US 2015/0344381 A1     Dec. 3, 2015

(30) Foreign Application Priority Data

Dec. 21, 2012  (DE) .................. 10 2012 112 964
Feb. 18, 2013  (DE) .................. 10 2013 101 575

(51) Int. Cl.
| | | |
|---|---|---|
| C07C 1/00 | (2006.01) | |
| C07C 1/20 | (2006.01) | |
| B01J 19/24 | (2006.01) | |
| C07C 7/00 | (2006.01) | |

(52) U.S. Cl.
CPC .............. C07C 1/20 (2013.01); B01J 19/24 (2013.01); C07C 7/005 (2013.01); B01J 2219/24 (2013.01); C07C 2529/40 (2013.01)

(58) Field of Classification Search
CPC .................................. C07C 1/22; C07C 1/20
USPC ........................................ 585/638, 639, 640
See application file for complete search history.

(56) References Cited

U.S. PATENT DOCUMENTS

| | | | |
|---|---|---|---|
| 4,387,263 A | 6/1983 | Vogt et al. | |
| 6,838,587 B2 * | 1/2005 | Lattner ................. | C07C 7/005 585/639 |
| 6,844,470 B2 | 1/2005 | Frater et al. | |
| 6,872,867 B1 | 3/2005 | Senetar | |
| 7,115,789 B2 * | 10/2006 | Kuechler ................ | C07C 1/20 585/259 |
| 7,132,580 B1 * | 11/2006 | Senetar ................... | C07C 1/20 585/639 |
| 7,855,312 B2 | 12/2010 | Borgmann et al. | |
| 7,919,660 B2 | 4/2011 | Vora et al. | |
| 2003/0125597 A1 | 7/2003 | Cheng et al. | |
| 2003/0139635 A1 | 7/2003 | Hack et al. | |
| 2004/0122272 A1 | 6/2004 | Van Egmond et al. | |
| 2004/0127758 A1 | 7/2004 | Van Egmond | |
| 2004/0267068 A1 | 12/2004 | Ding et al. | |
| 2004/0267069 A1 | 12/2004 | Ding et al. | |
| 2004/0267077 A1 | 12/2004 | Ding et al. | |
| 2006/0106270 A1 | 5/2006 | Glover et al. | |
| 2006/0135632 A1 | 6/2006 | Lattner et al. | |
| 2008/0242908 A1 | 10/2008 | McGlamery et al. | |
| 2008/0242910 A1 | 10/2008 | Kalnes et al. | |
| 2012/0083634 A1 | 4/2012 | Corradi | |

FOREIGN PATENT DOCUMENTS

| | | |
|---|---|---|
| DE | 10 2005 048931 | 4/2007 |
| EP | 0 088 494 | 9/1983 |
| WO | WO 2006 020083 | 2/2006 |
| WO | WO 2006 048098 | 5/2006 |
| WO | WO 2010 104579 | 9/2010 |

OTHER PUBLICATIONS

International Search Report for PCT/EP2013/075441, dated Feb. 20, 2014.

* cited by examiner

Primary Examiner — Sharon Pregler
(74) Attorney, Agent, or Firm — Justin K. Murray

(57) ABSTRACT

A process for producing olefins from oxygenates comprises the following steps:
(i) heterogeneously catalyzed conversion of at least one oxygenate to an entire stream containing liquid and gaseous organic compounds and water, and
(ii) separating the entire stream in a first separating means into a fraction containing at least 90 vol-% of the gaseous organic compounds of the entire stream, into a fraction containing at least 90 wt-% of the liquid organic compounds of the entire stream, and into a fraction containing at least 90 wt-% of the water of the entire stream.
Furthermore, the invention also comprises a plant for carrying out this process.

15 Claims, 1 Drawing Sheet

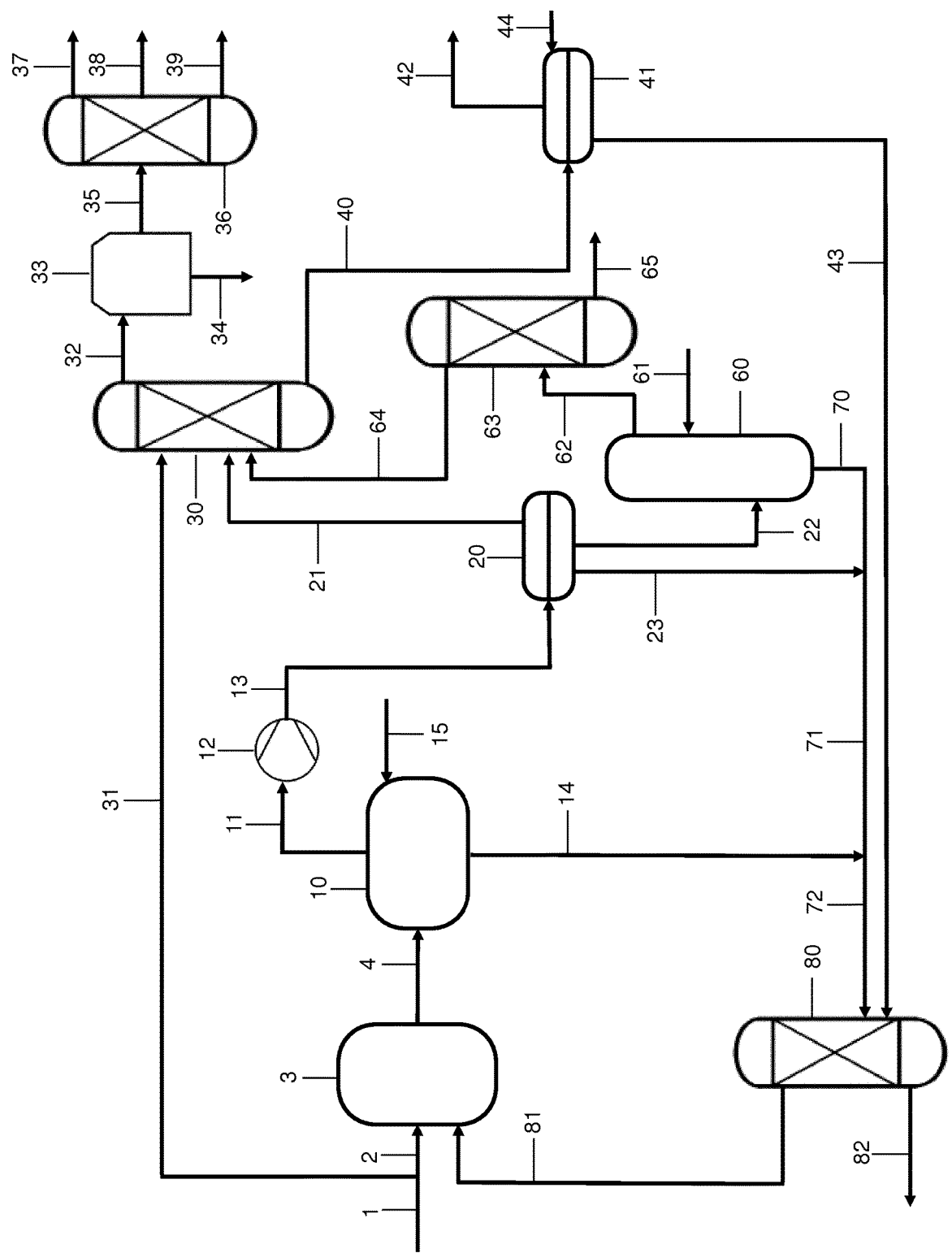

PROCESS AND PLANT FOR PRODUCING OLEFINS FROM OXYGENATES

CROSS REFERENCE TO RELATED APPLICATIONS

This application is a §371 of International PCT Application PCT/EP2013/075441, filed Dec. 3, 2013, which claims the benefit of DE102013101575.1, filed Feb. 18, 2013, and DE102012112964.9, filed on Dec. 21, 2012, all of which are herein incorporated by reference in their entireties.

TECHNICAL FIELD OF THE INVENTION

The invention relates to a process for producing olefins from oxygenates, which comprises the following steps: (i) heterogeneously catalyzed conversion of at least one oxygenate to a stream containing liquid and gaseous organic compounds and water, and (ii) separating the stream in a first separating means into three fractions.

BACKGROUND

Propene ($C_3H_6$), often also referred to as propylene, is one of the most important starting substances of the chemical industry. The demand for the base material propylene is increasing worldwide, wherein propylene just like ethylene mostly is produced from petroleum in a steam cracker in a ratio dependent on the process conditions and the raw materials.

To obtain additional propylene, a number of processes exist, such as the PDH process which proceeds from propane as educt. What is known, however, above all is the so-called MTP process, in which olefins are produced from methanol (MeOH) or dimethyl ether (DME) by catalytic conversion on a zeolitic catalyst. By varying the catalyst and the process conditions, the selectivity of the products obtained can be influenced and the product spectrum thus can be shifted towards short-chain olefins (then often also the process name Methanol-to-Olefin (MTO)), towards longer-chain products (then often also the process name Methanol-to-Gasoline (MTG)) or towards propylene.

The fundamentals of an MTP process are described for example in DE 10 2005 048 931 A1. From an educt mixture containing steam and oxygenates such as methanol and/or dimethyl ether, $C_2$ to $C_4$ olefins are produced above all. By a heterogeneously catalyzed reaction in at least one reactor, the educt mixture is converted to a reaction mixture comprising low-molecular olefins and gasoline hydrocarbons. By a suitable separation concept, higher olefins, above all the $C_{5+}$ fraction, can at least partly be recirculated into the reactor as recycling stream and in said reactor for the most part be converted to propylene, whereby the propylene yield is increased.

Due to the multitude of components obtained in the product spectrum, in particular the multitude of olefins obtained, the purification system of an MTP process mostly is very complex.

From US 2004/0122272 A1 it is known that in a first separating means the $C_{3-}$ fraction, an aqueous fraction as well as at least one $C_{4-}$ and $C_5$ fraction already are separated from each other. The $C_{3-}$ fraction then is processed further.

From U.S. Pat. No. 7,855,312 B2 it is known that first the oxygenates contained in the product stream are washed out via a water wash, before the individual carbon fractions are separated from each other.

U.S. Pat. No. 7,919,660 B2 describes how non-converted oxygenates, above all dimethyl ether, can be separated from light olefins, i.e. olefins with a small chain length, by means of a water wash.

According to WO 2010/104579 the light olefins obtained by the treatment are subjected to a water wash, wherein this wash can be effected at different points of the process.

WO 2006/048098 describes how a liquid fraction of hydrocarbons and oxygenates is charged to a first column in which the low boilers are separated from the high boilers. The separation of aqueous streams is not discussed.

From US 2003/0125597 A1 it is known to split up the olefin stream into a $C_{4+}$ fraction and a $C_{4-}$ fraction after cleaning the olefin stream from aqueous components. US 2012/0083634 A1 likewise teaches a process in which a light and a heavy stream rich in hydrocarbons is produced, wherein here a $C_2$ stream and a $C_{3+}$ stream are obtained. Here as well, the separation of the hydrocarbon streams is effected only after the removal of water.

From US 2008/0242908 A1 it is known that first the water can be removed and the remaining organic stream is separated into a $C_{3-}$ fraction and a $C_{4+}$ fraction and a third stream containing dimethyl ether.

US 2004/0267068 A1, US 2004/0267069 A1 and US 2004/0267077 A1 all discuss a similar separation concept, in which after passing a quenching system the hydrocarbon stream is subjected to a wash for removing the oxygenates, without previously or in this step a separation of the hydrocarbons being effected in dependence on their chain length.

US 2006/0135632 A1 describes the separation of the entire olefin stream from an aqueous fraction containing the oxygenates, without a detailed discussion of the further treatment of the olefins.

From U.S. Pat. No. 6,844,470 B2 a process is known, in which the $C_{4+}$ fraction is separated from the oxygenates in a first separating operation, and in a second separating operation the $C_{3-}$ fraction then is separated from the dimethyl ether in essence and the extracting agent used in this separating operation. In the first separating operation there can also be obtained a third stream containing the $C_{2-}$ fraction. In each of the two variants, however, contained water must already be separated previously.

US 2004/0127758 A1 finally describes a process for the purification of the mixture obtained from an MTP process, in which after a separate separation of the water, the stream rich in carbon is separated into a $C_{3-}$ fraction and a fraction containing $C_{4+}$ and dimethyl ether.

SUMMARY OF THE INVENTION

In all of the aforementioned processes, it is problematic that for the purification of the light olefins by distillation, above all for the purification of propylene and ethylene, temperatures below 0° C. must exist in the distillation. The light olefin streams therefore must be free from water, as otherwise a crystallization of water will occur in the head of the distillation column.

At the same time, however, it is of particular interest to separate the oxygenates during the processing of the olefin streams such that they can be subjected to a further purification. In this further purification, valuable oxygenates, above all the oxygenates used as educts such as methanol and dimethyl ether, must be separated from impurities such as e.g. higher ethers and ketones, so that the valuable oxygenates can be recirculated into the heterogeneously catalyzed conversion. A recirculation of the ethers and ketones not only renders the product processing more difficult, but also leads to undesired impurities which can reduce the catalyst life, which is why it is absolutely necessary to remove these components before a recirculation.

Therefore, it is the object underlying the invention to achieve an efficient separation of water and impurities from the olefin stream and at the same time separate the valuable oxygenates such that they can be recirculated into the heterogeneously catalyzed conversion.

This object is solved with embodiments of the present invention. In a first step, at least one oxygenate therefore is converted by heterogeneous catalysis to obtain an entire stream containing liquid and gaseous organic compounds and water. In a first separating means, this stream then is separated into three fractions, wherein the first fraction contains at least 90 vol-% of the gaseous organic compounds of the entire stream, the second fraction contains at least 90 wt-% of the liquid organic compounds of the entire stream, and the third fraction contains at least 90 wt-% of the water contained in the entire stream. This circuitry reduces both the total quantity of those hydrocarbons which must be subjected to a particularly expensive separation and the impurities which are contained in the gaseous organic compounds.

Preferably, the entire stream of the heterogeneously catalyzed conversion, which contains the organic compounds and water, is compressed after the heterogeneously catalyzed conversion (step (i)). This compression has the advantage that due to the adjusted pressures of 18 to 22 bar, preferably about 20 bar, it can be adjusted which compounds get into the first separating means in gaseous form and which in liquid form and there correspondingly become part of the respective fractions. The entire stream separated in the first separating means then is the product stream of the heterogeneously catalyzed conversion (step (i)) after the compression.

Furthermore, it was found to be advantageous to quench the entire stream, which contains organic compounds and water, yet before the compression. In that water here is guided into the product stream originating from the heterogeneously catalyzed conversion, parts of the impurities already can be extracted from the product mixture. In addition, the entire stream is cooled to 35 to 45° C., preferably about 40° C. The entire stream separated in the first separating means then is the product stream of the heterogeneously catalyzed conversion (step (i)) after the quench, preferably after the quench and a compression effected after the quench.

In a preferred aspect of the invention, the at least 90 vol-% of the gaseous hydrocarbons, which have been obtained in the first separating means (step (ii)), are separated in a second separating means into a fraction containing the $C_{3-}$ compounds and water and a stream containing the $C_4$ compounds and oxygenates. This leads to an optimized purification of the $C_{3-}$ hydrocarbon stream, which also contains the target product propylene.

Preferably, an extractive distillation is carried out in the second separating means, in order to further increase the separation efficiency. In a particularly preferred embodiment of the invention, methanol is used as extracting agent, which has the advantage that no substances foreign to the process are introduced into the process. This methanol favorably can originate from the methanol used as educt stream.

Preferably, the second separating means is designed as column such that above the extraction zone a distillation region is provided, in which the extracting agent, e.g. methanol, can be separated. This configuration has the advantage that there can also be used an extracting agent which still contains water, as in the distillation region above the extraction zone the top product of the extractive distillation is liberated both from the extracting agent and from water and the partly purified product thus is not again contaminated with water.

Furthermore, it was found to be advantageous to dry the fraction obtained in the second separating means, which contains the $C_{3-}$ compound and water, in a third separating means, so that the water still contained, whose quantities lie in the range from 10 to 50 ppm, is removed. Thus, a high-purity $C_{3-}$ fraction with a water content below 5 ppm is left.

Preferably, this fraction containing the $C_3$ compounds is separated by distillation in a fourth separating means into an ethylene fraction, a propylene fraction and a propane fraction. The olefins thus obtained have a degree of purity which is suitable for the further processing in a polymerization.

Furthermore, it was found to be advantageous to supply the fraction containing $C_4$ compounds and oxygenates from the second separating means to a fifth separating means, in which the $C_4$ fraction is separated from the oxygenates, so as to obtain the valuable oxygenates for a recirculation into the heterogeneously catalyzed conversion (step (i)).

Preferably, this separation is effected via a water wash, wherein the washing water has a temperature between 10 and 40° C. The oxygenates then are discharged together with the water stream, whereas the $C_4$ fraction is separated in very pure form and can be discharged as LPG product (liquefied gas).

According to the invention, the stream containing at least 90 wt-% of the liquid organic compound in addition is separated in a sixth separating means into a fraction containing at least 90 wt-%, preferably about 99 wt-% of the hydrocarbons of the stream and into a fraction containing at least 50 wt-%, preferably about 90 wt-% of the water content of the stream.

Preferably, this separation in the sixth separating means is designed as water wash. For this purpose, the hydrocarbon condensate obtained at a low condensation temperature is liberated from a considerable part of the impurities and oxygenates by a cold water wash, preferably with a washing water temperature between 10 and 40° C. This represents a very favorable form of the separation, since the high energy costs of a distillation are not incurred.

In an advantageous aspect of the invention, the stream containing at least 90 wt-% of the hydrocarbons from the sixth separating means is supplied to a seventh separating means, in which a $C_{4-}$ fraction is separated from a $C_{4+}$ fraction.

Advantageously, the $C_{4-}$ fraction of a processing stage is supplied to the fraction containing at least 90 vol-% of the gaseous hydrocarbons, wherein this supply in a particularly preferred way is effected into the second separating means. As a result, valuable products obtained, in particular propylene, can be separated and be obtained with a corresponding degree of purity.

The $C_{4+}$ fraction from the seventh separating means is discharged from the process. There is obtained the so-called MTP gasoline, which likewise represents a valuable product of the process.

Furthermore, it was found to be advantageous when water and/or oxygenates from the quench, the step (ii), from the first separating means, the fifth separating means and/or the sixth separating means are supplied to an eighth separating means in which water and oxygenates are at least partly separated from each other. As a result, valuable oxygenates which are suitable as educt can be purified.

In a particularly preferred aspect, the water and/or the oxygenates are at least partly recirculated into the step (i). The effectiveness of the process thereby can be increased.

Particularly preferably, the heterogeneously catalyzed conversion (step (i)) is effected in a two-stage process, wherein in the first stage the at least one oxygenate first is/are converted to at least one corresponding ether and in the second stage the ether(s) is/are converted to olefins. When methanol is used as oxygenate, a conversion of the methanol to dimethyl ether first is effected and subsequently the conversion of the dimethyl ether to propylene and other olefins, in particular also to aromatics and cyclic olefins. In this two-stage configuration it is recommendable to recirculate the oxygenate, preferably the methanol, already to before the first stage, i.e. before the conversion to dimethyl ether, while the vaporous water is introduced between the first and the second stage, as it must first be used as educt for the conversion of the ether to olefins. Thus, in the first stage there is used no unnecessary water which negatively influences the equilibrium reaction during the etherification, but the steam is available for the optimization of the process management of the olefin formation.

Finally, embodiments of the present invention can also include a plant. Such plant is particularly useful for carrying out a process according to any of the embodiments described herein. In one embodiment, this plant contains at least one reactor for the heterogeneously catalyzed conversion of at least one oxygenate to a stream containing liquid and gaseous organic compounds and water as well as a separating means for separating the entire stream containing liquid and gaseous organic compounds and water into a fraction containing at least 90 vol-% of the gaseous organic compounds of the entire stream, into a fraction containing at least 90 wt-% of the liquid organic compounds of the entire stream, and into a fraction containing at least 90 wt-% of the water of the entire stream.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

The FIGURE shows an embodiment of the present invention.

Further developments, advantages and possible applications of the invention can also be taken from the following description of the FIGURE. All features described and/or illustrated form the subject-matter of the invention per se or in any combination, independent of their inclusion in the claims or their back-reference.

In the drawing:

The FIGURE shows a schematic flow diagram of the process according to the invention.

The FIGURE schematically shows the procedure of the process according to the invention. For this purpose, an oxygenate, preferably methanol, is introduced into a reactor 3 via a conduit 1 and conduit 2. As heterogeneous catalyst a molecular sieve is used, preferably a zeolite, quite preferably a ZSM-5. The product obtained in the reactor 3 is discharged via conduit 4.

The entire product stream from conduit 4 subsequently flows into a quenching system 10, into which water is fed via conduit 15. From this quench, the quenching water in which already contained impurities have dissolved in part, is discharged via conduit 14. The remaining entire product stream is supplied to a compressor 12 via conduit 11 and after the compression to about 20 bar supplied to a first separating means 20 via conduit 13. This first separating means 20 preferably is designed as simple phase separator, whereby the current operating costs can greatly be lowered, since the high energy demand of a distillation is not required.

From the first separating means 20, a fraction containing at least 90 vol-% of the gaseous organic compounds of the quenched and compressed stream is introduced into a second separating means 30 via conduit 21. This second separating means 30 preferably is equipped as extractive distillation and utilizes methanol as extracting agent. This extracting agent originates from conduit 1 and is introduced into the column 30 via conduit 31.

Via conduit 32, the top product of the distillation column 30, which contains the $C_{3-}$ fraction and very small amounts of water, is supplied to a third separating means 33, preferably to a drier. In this drier 33, the water still contained is removed via conduit 34, and via conduit 35 the remaining $C_{3-}$ fraction is supplied to a fourth separating means 36, preferably to a distillation. From this distillation means 36, three streams which contain high-purity ethylene (conduit 37), high-purity propylene (conduit 38) and propane (conduit 39) are discharged.

Via conduit 40, the bottom product of the second separating means 30 is supplied to a fifth separating means 41. Preferably, the fifth separating means 41 is a separator, particularly preferably a scrubber, into which water is introduced via conduit 44 (to be added in the FIGURE). The purified $C_4$ stream is discharged via conduit 42, while the stream containing water and possibly also oxygenates is discharged from the fifth separating means 41 via conduit 43.

Furthermore, the stream containing at least 90 wt-% of the liquid organic fractions of the entire stream is supplied from the separator 20 via conduit 22 to a sixth separating means 60. This sixth separating means 60 also preferably is a water wash, wherein the washing water is introduced via conduit 61. A stream containing at least 90 wt-% of the hydrocarbons of the liquid stream is withdrawn from the top of the sixth separating means 60 and supplied to a seventh separating means 63.

The seventh separating means 63 preferably likewise is a distillation column and separates the $C_{4-}$ fraction from the $C_{4+}$ fraction. The $C_{4+}$ fraction is discharged from the process. The $C_{4-}$ fraction is supplied to the second separating means 30, so that valuable products contained therein can be recovered.

Together with the washing water, the stream containing water and oxygenates from the sixth separating means 60 is guided into an eighth separating means 80 via conduits 70, 71 and 72. By means of this eighth separating means 80 process water can be discharged, which is utilized for example for steam generation or also is supplied to the final water treatment. Via conduit 81, a stream containing the oxygenates and in part also water is supplied to the reactor 3 over the head. Via conduit 82, an aqueous waste stream is discharged.

Moreover, via conduit 23 the stream containing at least 90 wt-% of the total water content from the first separating means 20 can be introduced into conduit 70, via conduit 14 an aqueous stream from the quench 10 additionally can be introduced into conduit 71 and get into the eighth separating means 80 via conduit 72.

Via conduit 43, the stream containing water and oxygenates from the fifth separating means 41 also gets into the eighth separating means 80.

Although eight separating means 20, 30, 33, 36, 41, 60, 63, 80 are provided in the described exemplary embodiment according to the drawing, it lies within the scope of the invention that depending on the embodiment individual or groups of separating means can be omitted, so that then for example the sixth or eighth separating means 60, 80 directly follows the first separating means 20.

For better clarity, the separation tasks of the separating means are summarized below.

Separation Tasks of the Individual Separating Means:

first separating means 20 separation into a fraction containing at least 90 vol-% of the gaseous organic compounds of the entire stream, into a fraction containing at least 90 wt-% of the liquid organic compounds of the entire stream, and into a fraction containing at least 90 wt-% of the water of the entire stream second separating means 30 separation of the $C_{3-}$ fraction from the fraction containing $C_{4-}$ and oxygenates from the fraction containing at least 90 vol-% of the gaseous organic compounds of the entire stream third separating means 33 separation of the water from the $C_{3-}$ fraction fourth separating means 36 separation of ethylene, propylene and propane from the $C_{3-}$ fraction fifth separating means 41 separation of the fraction containing $C_{4-}$ and oxygenates into a $C_{4-}$ fraction and a fraction containing water and oxygenates sixth separating means 60 separation of the fraction containing at least 90 wt-% of the liquid organic compounds of the entire stream, which contains undesired impurities and oxygenates, into a fraction containing at least 99 wt-% of the liquid hydrocarbons and into an aqueous fraction which contains at least 50 wt-% of the sum of the oxygenates seventh separating means 63 separating means for separating the $C_{4-}$ fraction from the $C_{4+}$ fraction from the fraction containing at least 90 wt-% of the hydrocarbons eighth separating means 80 separation of water from at least one stream containing oxygenates and water

LIST OF REFERENCE NUMERALS 1, 2 conduit
3 reactor
4 conduit
10 quench
11 conduit
12 compressor
13, 14 conduit
20 first separating means
21-23 conduit
30 second separating means
31, 32 conduit
33 third separating means
34, 35 conduit
36 fourth separating means
37-39 conduit
40 conduit
41 fifth separating means
42-44 conduit
60 sixth separating means
61, 62 conduit
63 seventh separating means
64, 65 conduit
70-72 conduit
80 eighth separating means
81, 82 conduit While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A process for producing olefins from oxygenates, the process comprising the steps of:
   (i) heterogeneously catalyzed conversion of at least one oxygenate to an entire stream containing liquid and gaseous organic compounds and water;
   (ii) separating the entire stream in a first separating means into a fraction containing at least 90 vol-% of the gaseous organic compounds of the entire stream, into a fraction containing at least 90 wt-% of the liquid organic compounds of the entire stream, and into a fraction containing at least 90 wt-% of the water of the entire stream;
   (iii) introducing the fraction containing at least 90 vol-% of the gaseous organic compounds of the entire stream in a second separating means comprising an extractive distillation column wherein the extractive distillation column is operated under condition effective for separating the fraction containing at least 90 vol-% of the organic compounds of the entire stream into a fraction containing $C_{3-}$ compounds and water and a fraction containing $C_4$ compounds and oxygenates; and (iv) drying the fraction containing the $C_{3-}$ compounds and water in a dryer to produce a stream of water and a stream containing the $C_{3-}$ compounds.

2. The process according to claim 1, wherein after step (i) the entire stream is compressed.

3. The process according to claim 2, wherein the entire stream is quenched before being compressed.

4. The process according to claim 1, wherein from the stream containing the $C_{3-}$ compounds an ethylene fraction, a propylene fraction and a propane fraction are separated by distillation in a fourth separating means.

5. The process according to claim 1, wherein from the fraction containing the $C_4$ compounds and oxygenates the $C_4$ compounds are separated from the oxygenates in a fifth separating means.

6. The process according to claim 5, wherein the separation of the $C_4$ compounds from the oxygenates is effected by water wash in the fifth separating means and the oxygenates are discharged together with the water.

7. The process according to claim 1, wherein from the fraction containing at least 90 wt-% of the liquid organic compounds of the entire stream, a stream containing at least 90 wt-% of the hydrocarbons of this fraction and an aqueous stream, which contains at least 50 wt-% of the oxygenates, are separated from each other in a sixth separating means.

8. The process according to claim 7, wherein the separation of the fraction containing at least 90 wt-% of the liquid organic compounds of the entire stream is effected by a water wash and contained oxygenates are discharged from the sixth separating means together with the washing water.

9. The process according to claim 7, wherein the stream containing at least 90 wt-% of the hydrocarbons of the fraction is separated into a $C_{4-}$ fraction and a $C_{4+}$ fraction in a seventh separating means.

10. The process according to claim 6, wherein the stream of a processing stage containing the $C_{4-}$ fraction is supplied to the fraction containing at least 90 wt-% of the gaseous hydrocarbons of the entire stream.

11. The process according to claim 1, wherein the streams containing water and/or oxygenates from the quench, the step (ii) or the first, the fifth and/or the sixth separating means are supplied to an eighth separating means in which water and oxygenates are at least partly separated from each other.

12. The process according to claim 11, wherein water and/or oxygenates from the eighth separating means separating water and oxygenates are at least partly recirculated into the step (i).

13. A process for producing olefins from oxygenates, the process comprising the steps of:

reacting an oxygenate in a reactor under conditions effective for heterogeneously catalytically converting the oxygenate into an aqueous reactor stream comprising liquid and gaseous organic compounds;

quenching the aqueous reactor stream and then compressing the aqueous reactor stream in a compressor to produce a pressurized aqueous reactor stream;

separating the pressurized aqueous reactor stream in a first phase separator configured to produce a first gaseous stream, a first water stream, and a first liquids stream, wherein the first gaseous stream contains at least 90 vol-% of the gaseous organic compounds of the pressurized aqueous reactor stream, wherein the first liquids stream contains at least 90 vol-% of the liquid organic compounds of the pressurized aqueous reactor stream, wherein the first water stream contains at least 90 vol-% of the water of the pressurized aqueous stream;

introducing the first gaseous stream into an extractive distillation column using methanol as an extracting agent, wherein the extractive distillation column is operated under conditions effective for producing a second gaseous stream and a second bottoms stream, wherein the second gaseous stream consists essentially of $C_{3-}$ and water, wherein the second bottoms stream consists essentially of $C_{4-}$ oxygenates and water, introducing the second gaseous stream into a dryer under conditions effective for removing the water from the second gaseous stream to produce a dried $C_{3-}$ stream; and introducing the dried $C_{3-}$ stream to a distillation means under conditions effective for separating the dried $C_{3-}$ stream into ethylene, propylene, and propane.

14. The process according to claim 13, further comprising the step of introducing the first liquids stream into a sixth separating means under conditions effective for producing a top gas comprising at least 90 wt-% of the hydrocarbons of the first liquids stream, wherein the sixth separating means comprises a water wash.

15. The process according to claim 14, further comprising the step of introducing the top gas from the sixth separating means to a seventh separating means that is configured to produce a top stream comprising a C4− fraction and a bottoms stream comprising a C4+ fraction, wherein the top stream is then introduced to the extractive distillation column for separation therein, wherein the seventh separating means comprises a distillation column.

* * * * *